Figure 1:
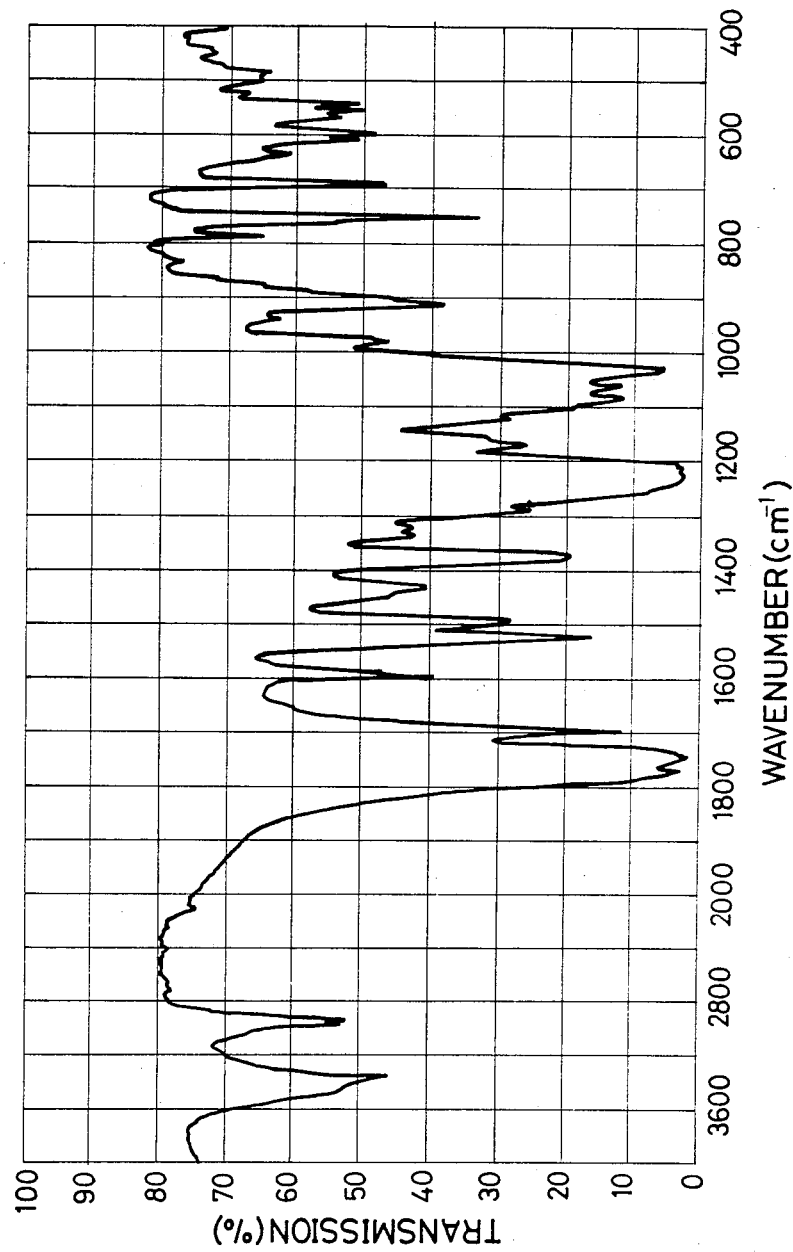

United States Patent [19]

Muto et al.

[11] Patent Number: 4,540,689

[45] Date of Patent: Sep. 10, 1985

[54] PENICILLIN DERIVATIVE

[75] Inventors: Shigeaki Muto, Tokyo; Kouichi Niimura, Sayama; Takao Ando; Akihiko Kanno, both of Tokyo; Takao Furusho, Machida; Chikao Yoshikumi, Kunitachi, all of Japan

[73] Assignee: Kureha Kagaku Kogyo Kabushiki Kaisha, Nihonbashi, Japan

[21] Appl. No.: 418,760

[22] Filed: Sep. 16, 1982

[30] Foreign Application Priority Data

Sep. 22, 1981 [JP] Japan .................. 56-149869
Sep. 22, 1981 [JP] Japan .................. 56-149870

[51] Int. Cl.$^3$ .................. A61K 31/43; A61K 31/44; C07D 499/68; C07D 499/70
[52] U.S. Cl. .................. 514/196; 260/239.1; 514/194
[58] Field of Search .................. 260/239.1; 424/263, 424/271

[56] References Cited

U.S. PATENT DOCUMENTS

| B 547,208 | 2/1976 | Schmidt et al. | 260/239.1 |
|---|---|---|---|
| 4,317,775 | 3/1982 | Burri et al. | 260/239.1 |
| 4,327,105 | 4/1982 | Scalesciani | 260/239.1 |
| 4,342,768 | 8/1982 | Kellogg | 260/239.1 |

FOREIGN PATENT DOCUMENTS

| 1940571 | 2/1970 | Fed. Rep. of Germany . |
|---|---|---|
| 2086746 | 12/1971 | France . |
| 630264 | 10/1949 | United Kingdom . |
| 1081093 | 8/1967 | United Kingdom . |

OTHER PUBLICATIONS

Jansen et al., *Journal of the Chemical Society*, (1965), Part II, pp. 2127–2132.

Gomis et al., *Bulletin de la Societe Chimique de France*, (1968), No. 1, pp. 420–424.

Medicinal Chemistry, Burger, 3rd. Ed., Part 1, p. 400, Wiley-Interscience, New York, (1970).

*Primary Examiner*—Natalie Trousof
*Assistant Examiner*—Vera C. Clarke

[57] ABSTRACT

A penicillin derivative having an antibacterial activity similar to a penicillin antibiotic in a living body without affecting the intestinal bacterial colonies, a process for preparing the derivative and a pharmaceutical composition in a dosage unit form containing the derivative as an active ingredient are disclosed.

2 Claims, 8 Drawing Figures

PENICILLIN DERIVATIVE

The present invention relates to a compound derived from a penicillin and to a medicine containing the compound as an active ingredient. In particular, the present invention relates to a compound obtained by chemically modifying a penicillin, an antibacterial activity of the compound being lost by such a chemical modification but recovered when the compound is absorbed into a living body, and to a medicine containing the compound as an active ingredient and exhibiting a penicillin-like activity in the living body.

The eight figures of drawings illustrate in graphic form the infrared absorption bands for the compounds of Examples 1–8 herein, respectively.

Penicillins are well known as excellent antibiotics due to the selective toxicity to bacteria. However, the penicillin antibiotic has a serious defect, that is, it may disturb the beneficial bacterial colonies ordinarily present in living bodies, particularly the intestinal bacterial colonies, since it may be also antibacterially active against the beneficial bacteria. This defect is very serious when such an antibiotic is orally administered. As a result, "microbisme selectionné et substitué" is caused resulting in colitis and diarrhea.

It is an object of the present invention to provide an antibiotic without having this defect.

An another object of the present invention is to provide a compound which is useful as an active ingredient of the antibacterial medicine.

A still another object of the present invention is to provide a medicine exhibiting an antibacterial activity similar to a penicillin antibiotic in a living body.

A compound of the present invention (hereinafter referred to as the present compound) is derived from a penicillin and has the general formula (I):

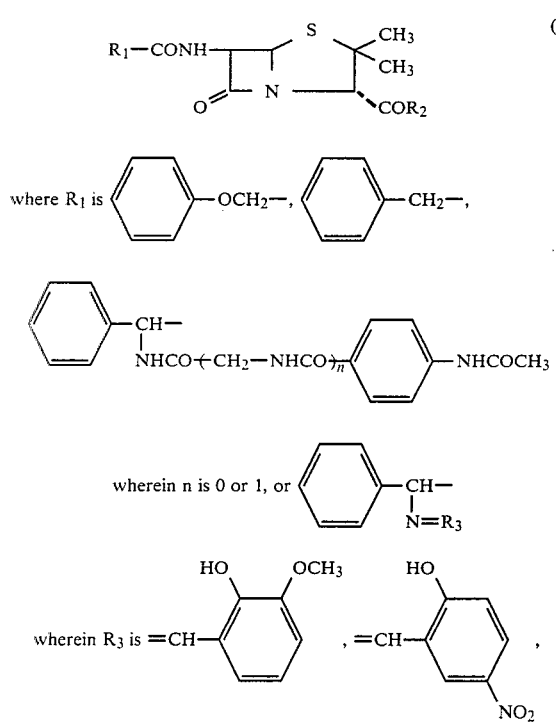

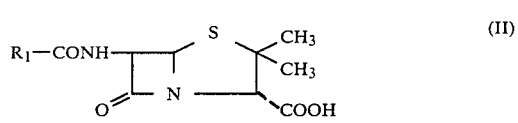

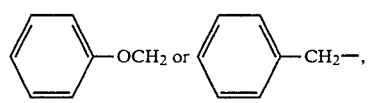

wherein $R_4$ is a hydrogen atom, an alkyl group having 1 to 4 carbon atoms or an alkali metal. The present compound may be in the form of a salt other than alkali metal salt, for example, an alkali earth metal salt, an aluminum salt, an ammonium salt and the like.

The present compound is derived from a penicillin antibiotic by a chemical modification. It is absorbed into a living body without affecting the bacterial colonies ordinarily present in living bodies and shows an antibacterial activity only when entering into blood, therefore, the present compound is an antibiotic of the new type quite different from the conventional penicillin antibiotics.

The present compound may be synthesized by the following process.

(1) Benzylpenicillanic acid or phenoxymethylpenicillanic acid having the general formula (II):

wherein $R_1$ is

[structures: phenyl-OCH$_2$ or phenyl-CH$_2$—,]

or a salt thereof is dissolved in an organic solvent, for example, benzene, tetrahydrofuran, dimethylformamide, dichloromethane, pyridine, dicyclohexylamine, acetone, triethylamine, chloromethane, dioxane, methanol, ethanol, water, ether and the like. It is preferable to add an activating agent, for example, carbodiimide, ethyl chloroformate, oxalyl chloride and the like. Then into the thus-prepared solution, a compound having the general formula (III):

$$R_2'X \qquad (III)$$

wherein $R_2'$ is

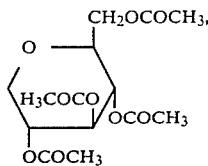

—R$_4$ or —CH$_2$OR$_4$ wherein R$_4$ is the same meaning as above, and X is chlorine or bromine, in an amount more than equimolar with benzylpenicillanic acid, phenoxymethylpenicillanic acid or a salt thereof is added. The whole system is brought into reaction at the temperature of −30° to +50° C. for 1 minute to 48 hours. After the reaction is over, the present compound is collected by the conventional method such as extraction with a solvent, washing with a solvent, recrystallization and the like.

(2) Phenylglycinopenicillanic acid having the general formula (IV):

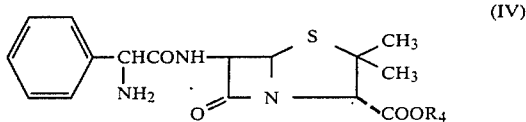

wherein R$_4$ is the same meaning as above, or a salt thereof is dissolved in an organic solvent such as alcohol at the temperature of −10° to +50° C. Then into the thus-prepared solution, a compound having the formula (V):

wherein R$_3$ is the same meaning as above, is added. The whole system is brought into reaction at the temperature of −30° to +50° C. for 1 minute to 10 hours. After the reaction is over, the present compound is collected by the conventional method such as extraction with a solvent, washing with a solvent, recrystallization and the like.

(3) 7-(alpha-D-phenylglycine)penicillanic acid having the formula (VI):

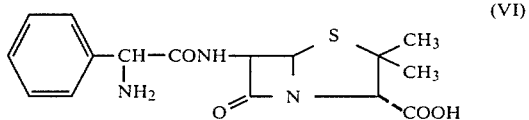

or a derivative thereof is added drop by drop into a solution of a compound having the general formula (VII):

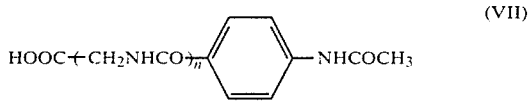

wherein n is 0 or 1, and carbodiimide in tetrahydrofuran. The thus-prepared solution is brought into reaction at the temperature of −30° to +50° C. for 0.5 to 48 hours. After the reaction is over, the present compound is collected by the conventional method such as extraction with a solvent, washing with a solvent, recrystallization and the like.

As seen from Examples described below, the present compound has low toxicity and exhibits an antibacterial activity in a living body without affecting the intestinal bacterial colonies.

The present compound can be useful in the same field as the conventional penicillin antibiotics since the present compound is transformed into a penicillin antibiotic in a living body.

The present compound can be used in a dosage unit form such as a drug or a pharmaceutical composition. The composition may contain 0.01 to 99.5% by weight, generally 0.1 to 90% by weight of the present compound as an active ingredient.

The pharmaceutical composition may contain a pharmaceutically acceptable carrier, diluent or adjuvant as well as at least one of the present compound. Further, the composition may contain filler, extender, binder, wetting agent, disintegrant, retarder of dissolution, accelerator of reabsorption, adhesive carrier and/or lubricant, for example, starch, mannitol, silicic acid, cellulose derivative, gelatin, alginate, glycerol, agar, calcium carbonate, sodium hydrogen carbonate, paraffin, quartarnary ammonium compound, glycerol monostearate, kaolin, bentonite, talc, aluminum stearate, magnesium stearate, polyethylene glycol and the like.

The pharmaceutical composition may be administered orally or rectally or by injection. The dosage form for oral administration may be tablet, capsule, powder, granule, pill, ampoule or the like. The composition may be in the form of pharmaceutically acceptable emulsion, solution, suspension and the like.

A syrup or elixir may contain an inert diluent such as water and paraffin and may be used as a liquid composition suitable for oral administration. These composition may contain an adjuvant such as wetting agent, edulcorant and seasoning agent.

A suppository containing the present compound as an active ingredient may contain polyethylene glycol and/or fatty acid or ester thereof.

The pharmaceutical composition for injection may be a stearilized aqueous or nonaqueous solution, suspension or emulsion and may contain, for example, propylene glycol, polyethylene glycol, olive oil and the like.

The present compound may be useful for the same as the conventional penicillin antibiotics and effective in treating an infectious disease due to bacteria such as Streptococcus, Pneumococcus, Gonococcus, diphteria bacillus, Staphylococcus, Spirochaeta, Actinomyces, Shigella, E. coli, Myxomycetes, Enterecoccus, Meningococcus and the like. The diseases to be able to be treated with the present compound is exemplified as follows; tonsil, pharyngitis,laryngitis, wound, burn, postoperative secondary infection, lymphadenitis, septicemia, bacterial endocarditis, pneumonia, pulmonary suppuration, bronchitis, scarlet fever, gonorrhea, cystitis, pyothorax, urethritis, bacterial dysentery, meningitis, diphtheria, otitis media, carbuncle, actinomycosis and the like.

The dose of the drug of the pharmaceutical composition of the present compound may depend on the degree of the infection and the condition of the patient, and generally the dose of 0.1 to 10 g may be administered to an adult patient per one day, divided into several times.

The invention is illustrated in more detail in the Examples which are not considering as limiting. It is apparent that many modifications and variations of the present invention may be made without departing from the spirit and scope thereof.

SYNTHESES OF THE PRESENT COMPOUNDS

EXAMPLE 1

Synthesis of the compound represented by the following formula

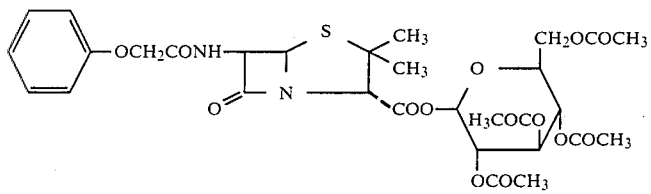

Into a solution of 776 mg of phenoxymethylpenicillin (free type) in 10 ml of dimethylformamide, 362 mg of dicyclohexylamine was added, and after about 5 min of the addition, 822 mg of tetraacetylbromoglucose was added to the mixture and the whole mixture was stirred for a night. Then, the reaction mixture was put into 100 ml of water, and the aqueous mixture was subjected to extraction two times with each 80 ml of ethyl acetate. After washing the extract with 50 ml of aqueous 1% solution of sodium hydrogen carbonate, and with 50 ml of water, the organic layer was dried on anhydrous magnesium sulfate. On evaporating the solvent from the thus dried extract, crystals educed. Recrystallizing the crystals from a mixed solvent of ethyl acetate and n-hexane, 884 mg of the present compound was obtained with a yield of 65%.

The characteristics of the present compound thus obtained were as follows:
(1) melting point; 162°–163.5° C.,
(2) elementary analysis;

|  | C (%) | H (%) | N (%) |
|---|---|---|---|
| theoretical: | 52.94 | 4.50 | 4.12 |
| experimental: | 52.8 | 4.4 | 4.1 |

(3) infrared absorption bands (KBr method); $v_{max}(cm^{-1})$: 1772, 1740, 1698; refer to FIG. 1.

EXAMPLE 2

Synthesis of the compound represented by the following formula

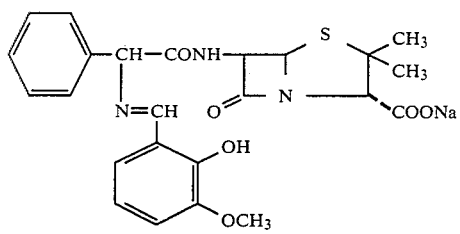

Into a solution of 3.71 g of sodium 6-phenylglycinopenicillanate in 50 ml of methanol, 3.1 g of 3-methoxysalicylaldehyde was added, and the mixture was stirred for 2 hours at room temperature. Then, the solvent was distilled off from the reaction mixture and the residue was dissolved in 5 ml of ethanol. After filtering, the filtrate was added dropwise into 200 ml of n-hexane under agitation. After leaving the mixture for one hour, the thus educed yellow crystals were collected by filtration, washed with 30 ml of n-hexane and dried at room temperature under a pressure of 0.1 mmHg for 4 hours to obtain 3.4 g of the product, sodium 6-(3-methoxysalicylaldehydeiminophenylglycino)penicillanate, with a yield of 67%.

The characteristics of the present compound thus obtained were as follows:
(1) melting point; 189°–193° C. (decomposition),
(2) elementary analysis;

|  | C (%) | H (%) | N (%) |
|---|---|---|---|
| theoretical: | 57.03 | 4.75 | 8.32 |
| experimental: | 56.92 | 4.74 | 8.30 |

Figure 2:
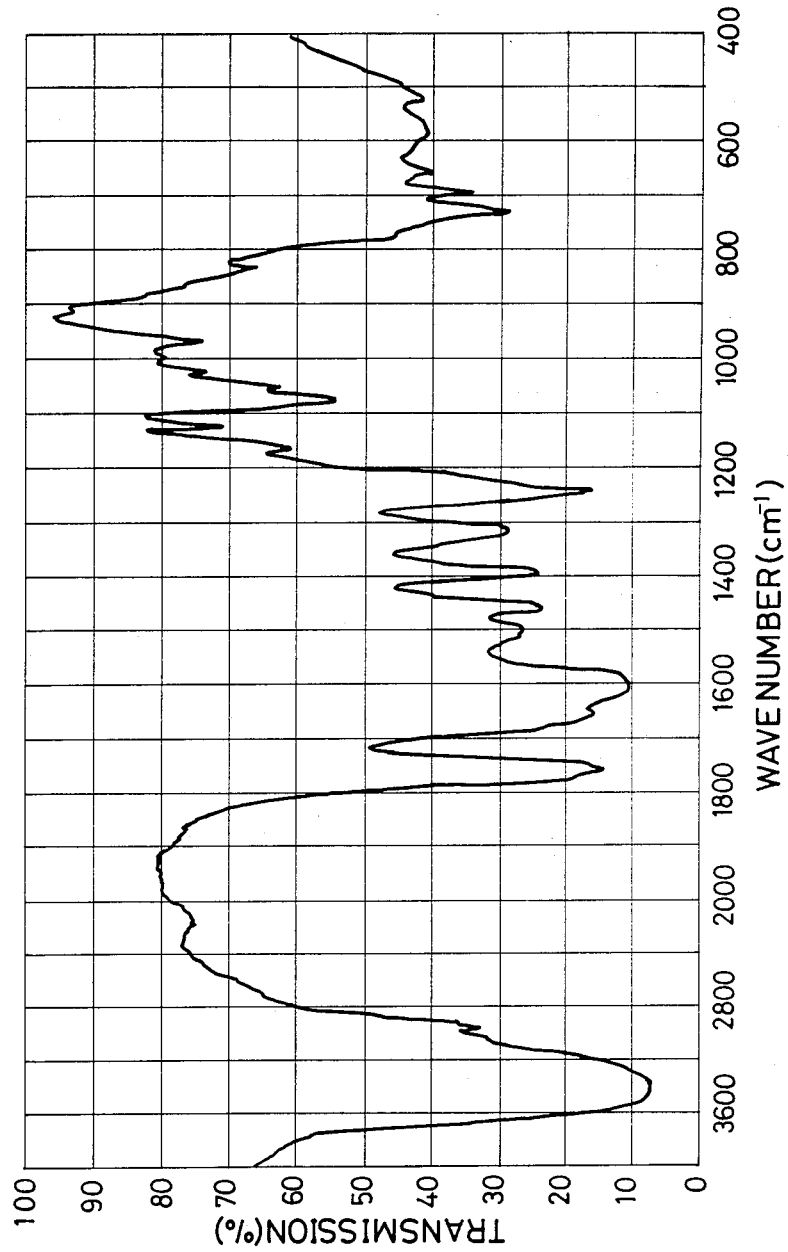

(3) infrared absorption bands (KBr method); $v_{max}(cm^{-1})$: 3400, 1760, 1655, 1610, 1245; refer to FIG. 2.

EXAMPLE 3

Synthesis of the compound represented by the following formula

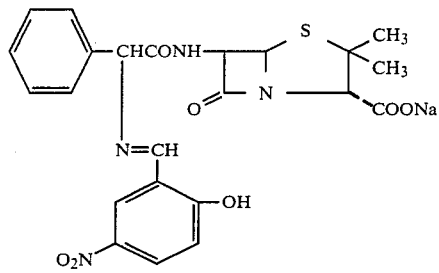

Into a solution of 3.71 g of sodium 6-phenylglycinopenicillanate in 50 ml of methanol, 3.2 g of 5-nitrosalicylaldehyde was added, and the mixture was stirred for 2 hours at room temperature. Then, the solvent was distilled off from the reaction mixture and the residue was dissolved in 5 ml of ethanol. The solution was filtered and the filtrate was added dropwise into 200 ml of n-hexane under agitation. After leaving the mixture for one hour, the thus educed yellow crystals were collected by filtration, washed with 30 ml of n-hexane and dried at room temperature under a reduced pressure of 0.1 mmHg for 4 hours to obtain 3.4 g of the crystals, sodium 6-(5-nitrosalicylaldehydeiminoglycino)penicillanate, with a yield of 65%.

The characteristics of the present compound thus obtained were as follows:
(1) melting point; 212°–214° C. (decomposition),
(2) elementary analysis;

|  | C (%) | H (%) | N (%) |
|---|---|---|---|
| theoretical: | 53.08 | 4.04 | 10.77 |
| experimental: | 52.97 | 4.01 | 10.71 |

Figure 3:
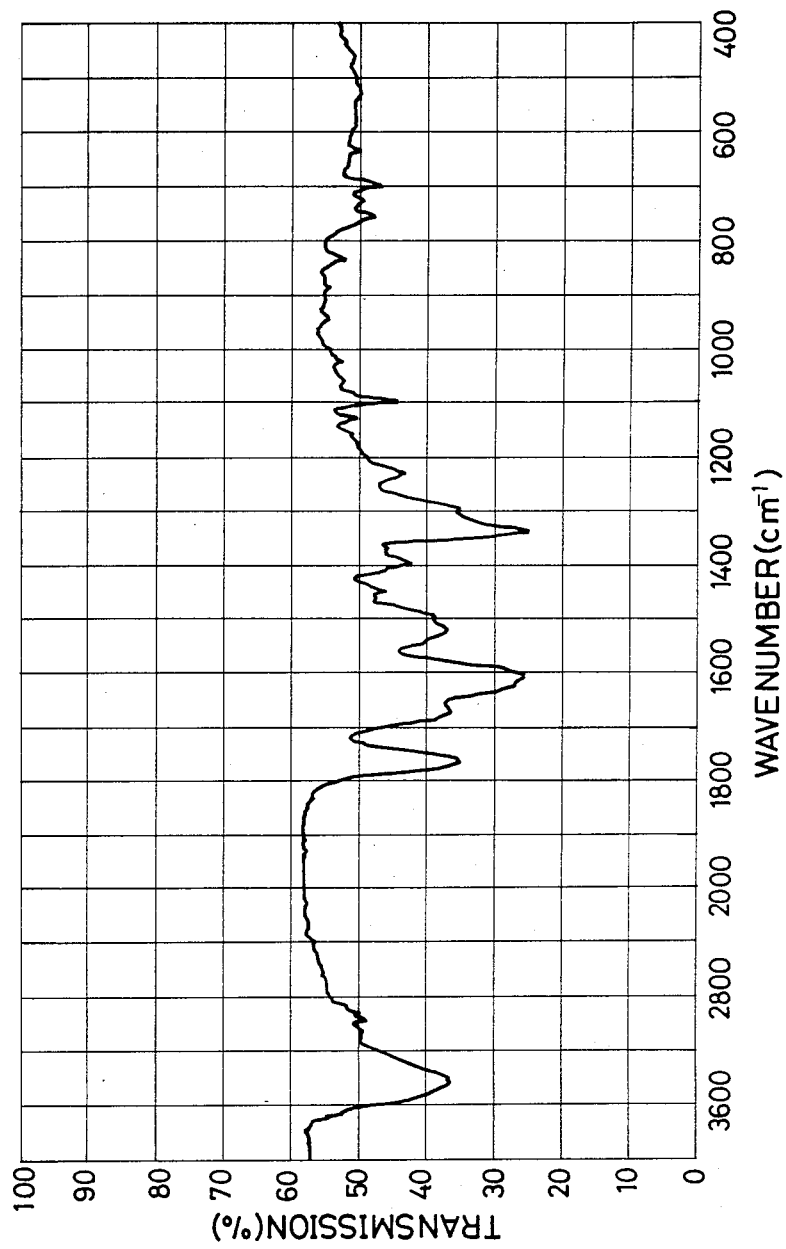

(3) infrared absorption bands (KBr method); $v_{max}(cm^{-1})$: 3420, 1767, 1673, 1608, 1340; refer to FIG. 3.

EXAMPLE 4

Synthesis of the compound represented by the following formula

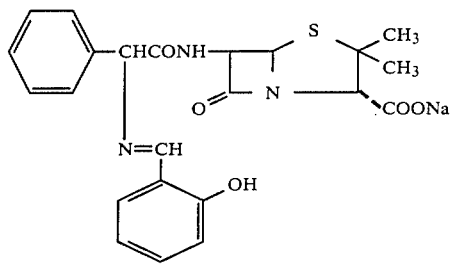

Into a solution of 3.71 g of sodium 6-phenyl-glycinopenicillanate in 50 ml of methanol, 3.0 g of salicylaldehyde was added, and the mixture was stirred for 2 hours at room temperature. After distilling off the solvent from the reaction mixture, the residue was dissolved in 5 ml of ethanol, and the solution was filtered. After adding the filtrate dropwise into 200 ml of n-hexane under agitation and leaving the mixture for one hour, the thus educed yellow crystals were collected by filtration, washed with 30 ml of n-hexane and dried at room temperature under a reduced pressure of 0.1 mmHg for 4 hours to obtain 3.4 g of the crystalline product, sodium 6-(salicylaldehydeiminophenyl-glycino)penicillanate, with a yield of 72%.

The characteristics of the present compound thus obtained were as follows:

(1) melting point; 198°-199° C. (decomposition),
(2) elementary analysis;

|  | C (%) | H (%) | N (%) |
|---|---|---|---|
| theoretical: | 58.11 | 4.63 | 8.84 |
| experimental: | 58.02 | 4.64 | 8.90 |

Figure 4:
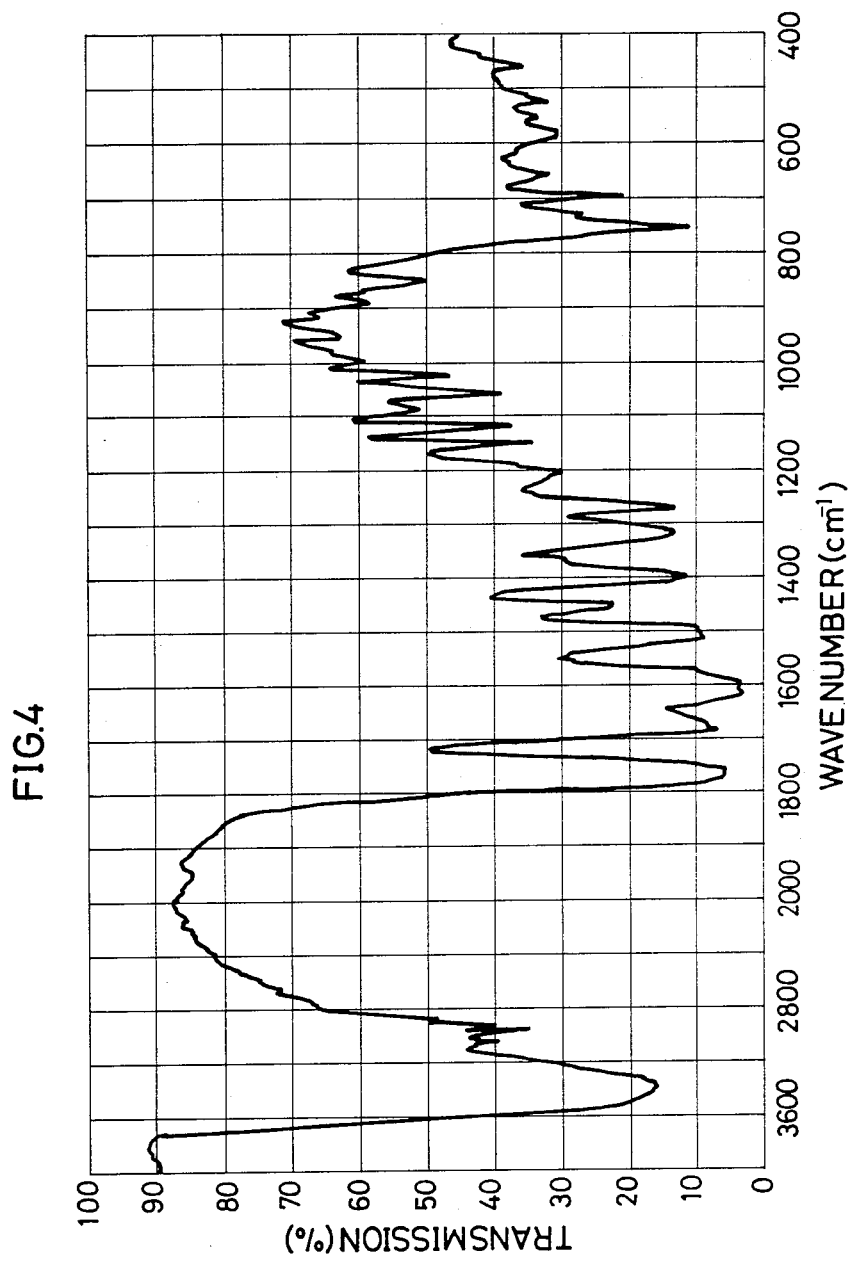

(3) infrared absorption bands (KBr method); $v_{max}(cm^{-1})$: 3400, 1775, 1687, 1620, 1595, 1515, 1400; refer to FIG. 4.

EXAMPLE 5

Synthesis of the compound represented by the following formula

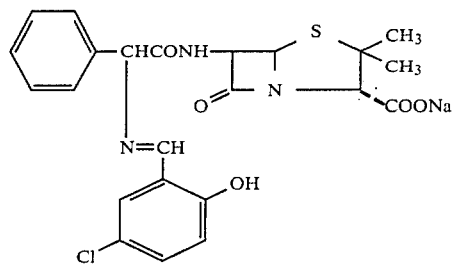

Into a solution of 3.71 g of sodium 6-phenyl-glycinopenicillanate in 50 ml of methanol, 3.1 g of 5-chlorosalicylaldehyde was added, and the mixture was stirred for 2 hours at room temperature. After distilling off the solvent from the reaction mixture, the residue was dissolved in 5 ml of ethanol, and the solution was filtered. After adding the filtrate dropwise into 200 ml of n-hexane under agitation and leaving the mixture for one hour, the thus educed yellow crystals were collected by filtration, washed with 30 ml of n-hexane and dried at room temperature under a reduced pressure of 0.1 mmHg for 4 hours to obtain 3.3 g of the crystalline product, sodium 6-(5-chlorosalicylaldehydeimino-phenylglycino)penicillanate, with a yield of 65%.

The characteristics of the present compound thus obtained were as follows:

(1) melting point; 203°-206° C. (decomposition),
(2) elementary analysis;

|  | C (%) | H (%) | N (%) |
|---|---|---|---|
| theoretical: | 54.93 | 4.12 | 8.24 |
| experimental: | 54.78 | 4.08 | 8.21 |

Figure 5:
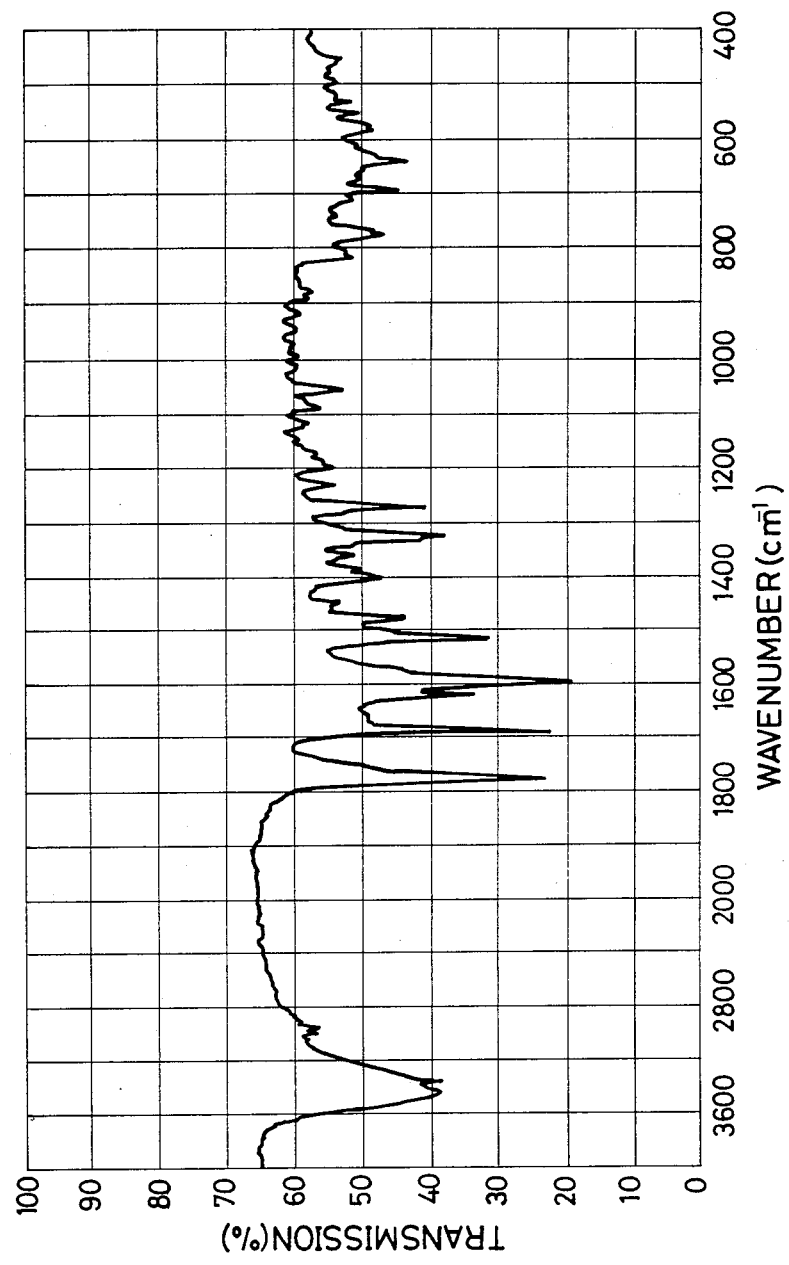

(3) infrared absorption bands (KBr method); $v_{max}(cm^{-1})$: 3450, 1775, 1689, 1598, 1518, 1323; refer to FIG. 5.

EXAMPLE 6

Synthesis of the compound represented by the following formula

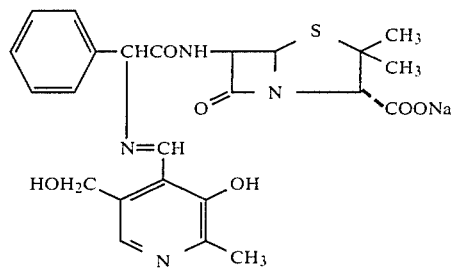

Into a solution of 3.71 g of sodium 6-phenyl-glycinopenicillanate in 50 ml of methanol, 1.67 g of pyridoxal was added, and the mixture was stirred for 2 hours at room temperature. After distilling off the solvent from the reaction mixture, the residue was dissolved in 5 ml of ethanol and the solution was filtered.

To the filtrate kept under agitation, 200 ml of n-hexane was added dropwise. After stirring the mixture for one hour, the thus educed yellow crystals were collected by filtration, washed with 30 ml of n-hexane and dried at room temperature for 4 hours under a reduced pressure of 0.1 mmHg to obtain 3.2 g of the purified product with a yield of 62%.

The characteristics of the present compound thus obtained were as follows:
(1) melting point; 188°–190° C. (decomposition),
(2) elementary analysis;

|  | C (%) | H (%) | N (%) |
| --- | --- | --- | --- |
| theoretical: | 55.38 | 4.81 | 10.77 |
| experimental: | 55.1 | 4.7 | 10.6 |

Figure 6:
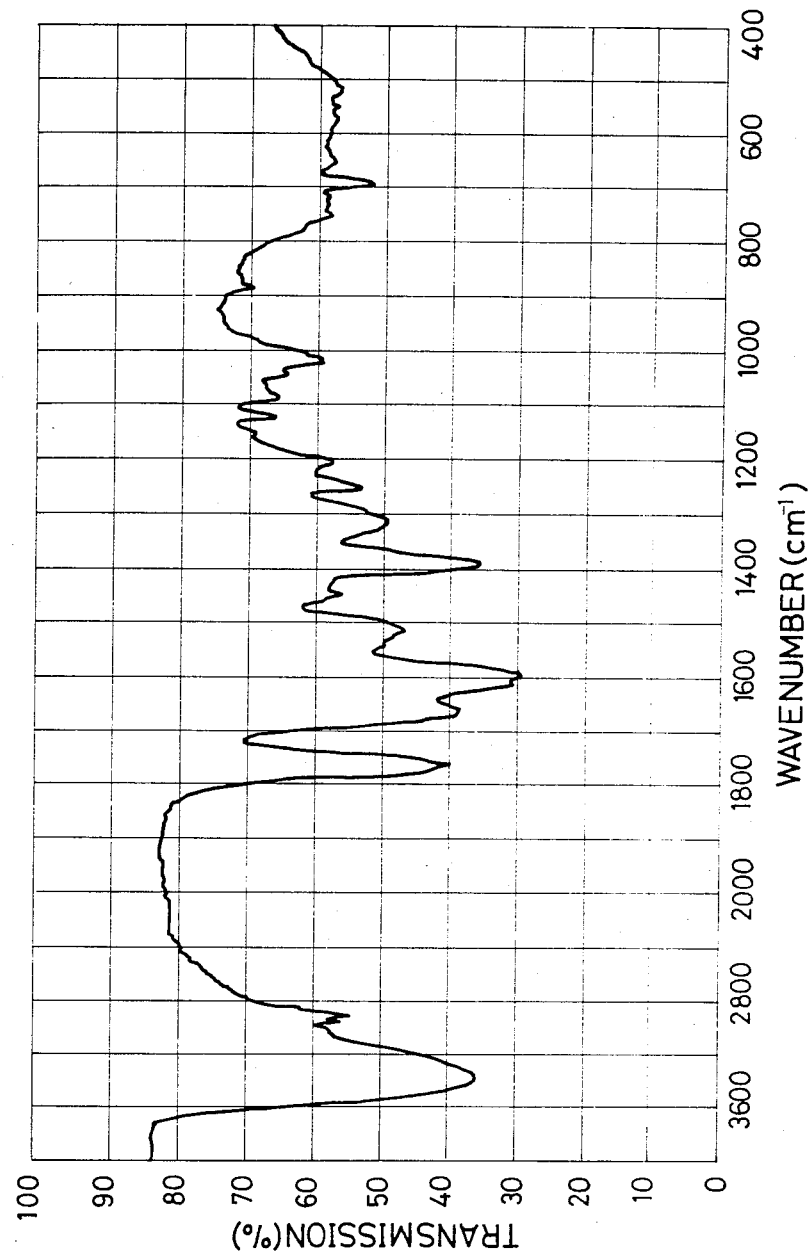

(3) infrared absorption bands (KBr method); $v_{max}(cm^{-1})$: 3400, 1760, 1660, 1595, 1392 refer to FIG. 6.

EXAMPLE 7

Synthesis of the compound represented by the following formula

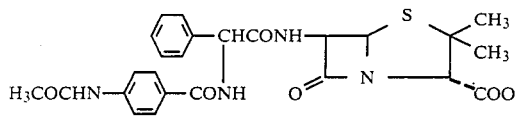

Into a solution of 0.90 g of N-acetyl-p-aminobenzoic acid and 1.05 g of dicyclohexylcarbodiimide in 100 ml of tetrahydrofuran, about 40 ml of aqueous solution containing 1.86 g of sodium 7-(alpha-D-phenylglycine)-penicillanate was added drop by drop while stirring, and the mixture was stirred for 24 hours at room temperature. After removing N,N'-dicyclohexylurea thus formed in the reaction mixture by filtration, the filtrate was subjected to distillation to evaporate off the solvent thereof, and the residue was mixed with 100 ml of water and the pH of the mixture was adjusted to 2 by the addition of aqueous 5% solution of hydrochloric acid. The thus separated solid material was extracted with 200 ml of ethyl acetate, washed three times with water and dried on anhydrous magnesium sulfate. Then the solvent was distilled off from the dried extract. Recrystallizing the residue from a mixed solvent of ethyl acetate and n-hexane, 0.59 g of white powdery crystals, 7-[N-(p-acetylaminobenzoicamido)-D-phenylglycineamido]penicillanic acid, were obtained with a yield of 21%.

The characteristics of the present compound thus obtained were as follows:
(1) melting point; 186°–188° C.,
(2) elementary analysis;

|  | C (%) | H (%) | N (%) |
| --- | --- | --- | --- |
| theoretical: | 58.82 | 5.01 | 10.98 |
| experimental: | 58.7 | 5.2 | 10.9 |

Figure 7:
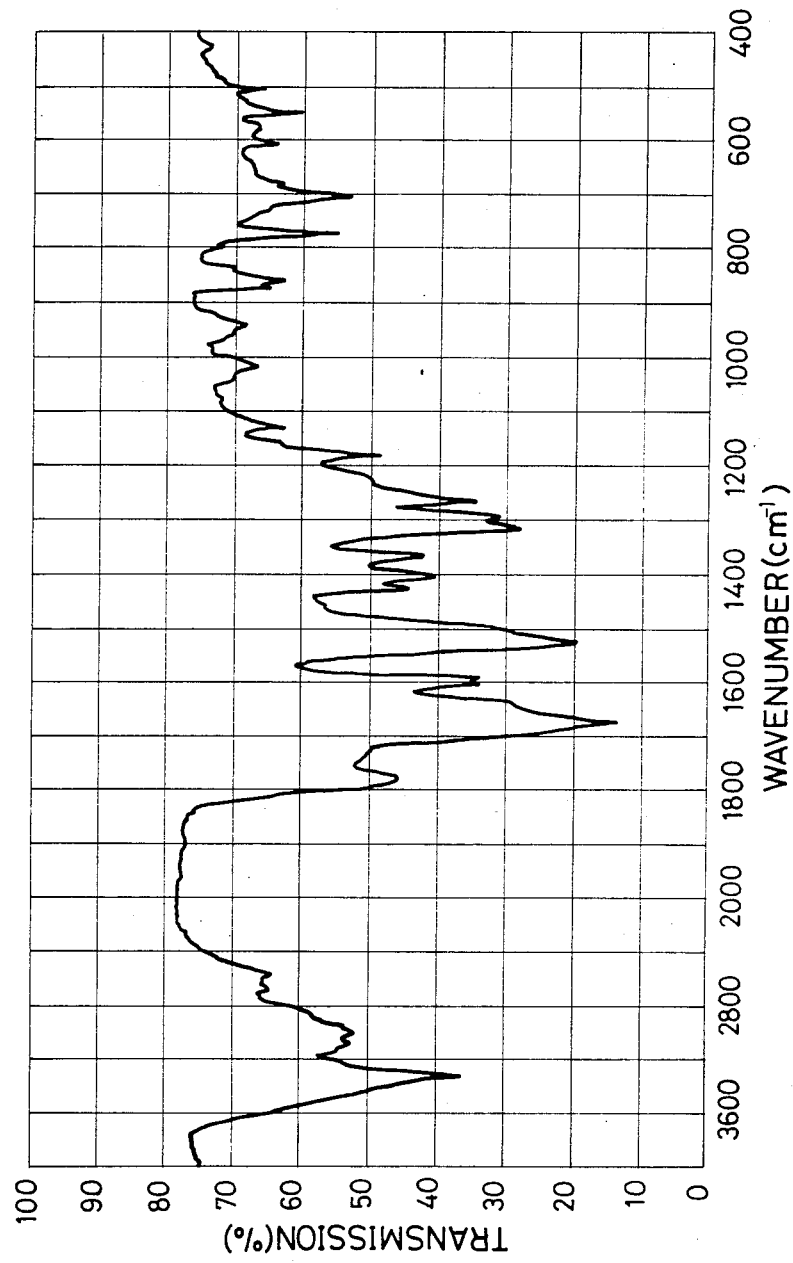

(3) infrared absorption bands (KBr method); $v_{max}(cm^{-1})$: 3320, 1780, 1673, 1527, 1315; refer to FIG. 7,
(4) ultraviolet absorption bands in acetonitrile; $v_{max}(nm)$: 236, 277

EXAMPLE 8

Synthesis of the compound represented by the following formula

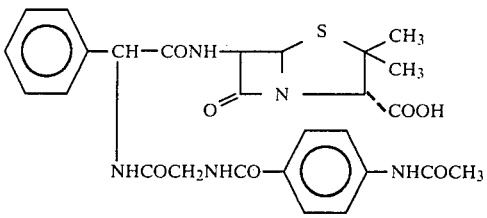

Into a solution of 1.18 g of N-acetyl-p-aminohippuric acid and 1.05 g of dicyclohexylcarbodiimide in 100 ml of tetrahydrofuran, about 40 ml of an aqueous solution of 1.86 g of sodium 7-(alpha-D-phenylglycine)penicillanate was added drop by drop while stirring, and the mixture was stirred for 24 hours at room temperature. After removing N,N'-dicyclohexylurea formed in the mixture by filtration, the solvent in the filtrate was distilled off. To the residue, 100 ml of water was added and the aqueous mixture was adjusted to pH of 2 by the addition of aqueous 5% solution of hydrochloric acid. The thus formed solid substance was subjected to extraction with 200 ml of ethyl acetate, and after washing the extract three times with water, the washed extract was dried on anhydrous magnesium sulfate, and the solvent was removed from the dried extract by distillation. Recrystallizing the residue from a mixed solvent of ethyl acetate and h-hexane, 0.81 g of white powdery crystals, 7-[N-(p-acetylaminohippuric acid amido)-O-phenylglycineamido]penicillanic acid, were obtained with a yield of 28%.

The characteristics of the present compound thus obtained were as follows:
(1) melting point; 176°–178° C.,
(2) elementary analysis;

|  | C (%) | H (%) | N (%) |
| --- | --- | --- | --- |
| theoretical: | 57.14 | 5.11 | 12.35 |
| experimental: | 57.1 | 5.2 | 12.4 |

Figure 8:
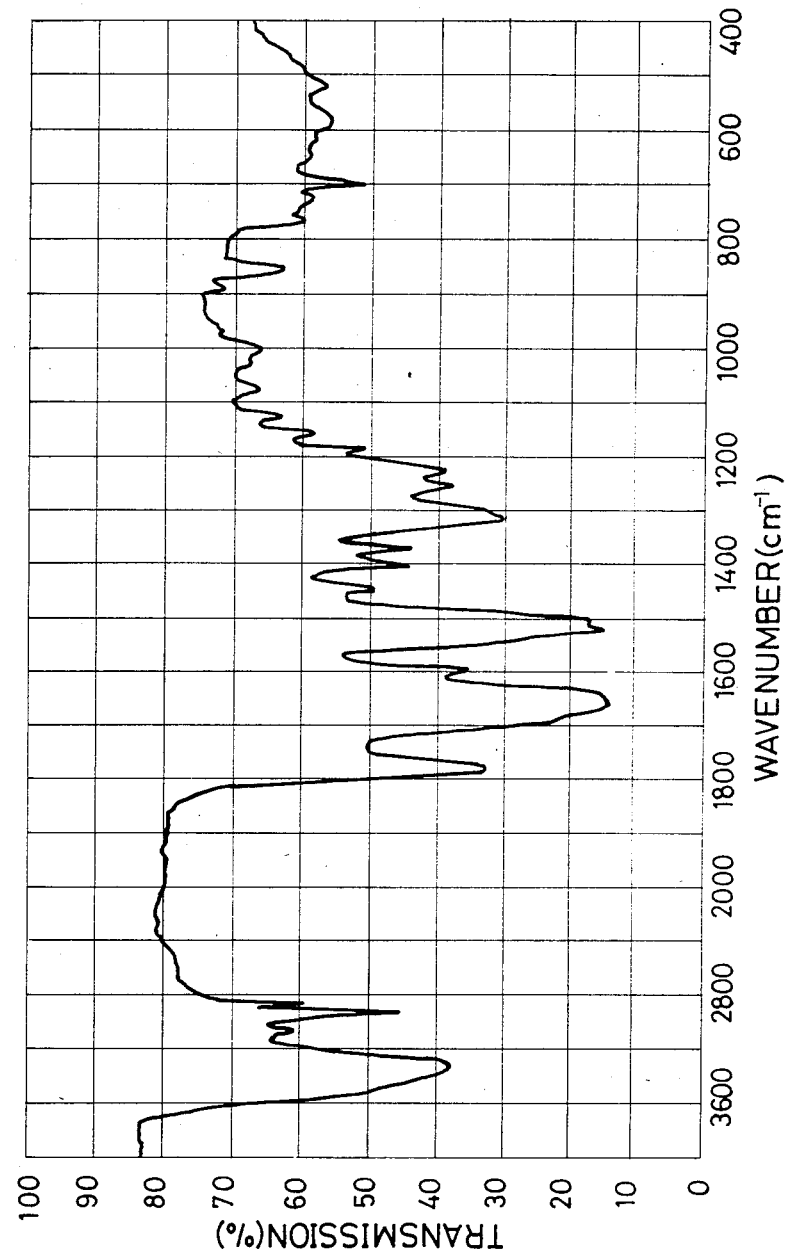

(3) infrared absorption bands (KBr method); $v_{max}(cm^{-1})$: 3325, 1778, 1660, 1525, 1503, 1313; refer to FIG. 8,
(4) ultraviolet absorption bands in acetonitrile; $\lambda_{max}(nm)$: 237, 279

EXAMPLE 9

Synthesis of the compound represented by the following formula

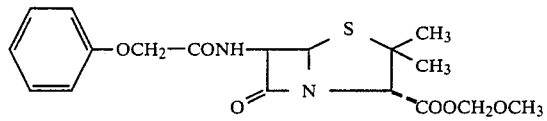

Into a solution of 776 mg of phenoxymethylpenicillin (free type) in 10 ml of dimethylformamide, 202 mg of triethylamine was added. To the thus yellow-coloured mixture, 500 mg of chloromethyl methyl ether was added, and the mixture was stirred for one hour. Then, the reaction mixture was put into 100 ml of water, and the mixture was subjected to extraction two times with each 80 ml of ethyl acetate. After washing the extract with 40 ml of water and dried on anhydrous magnesium sulfate, the solvent was distilled from the dried extract under a reduced pressure to obtain 521 mg of a crude product. Recrystallizing from a mixed solvent of ethyl acetate and n-hexane, 394 mg of the purified product was obtained with a yield of 50%.

The characteristics of the present compound thus obtained was as follows:

(1) elementary analysis;

|  | C (%) | H (%) | N (%) |
|---|---|---|---|
| theoretical: | 54.82 | 5.62 | 7.10 |
| experimental: | 54.7 | 5.6 | 7.0 |

EXAMPLE 10

Synthesis of the compound represented by the following formula

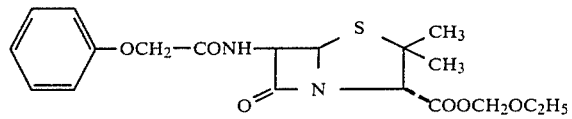

In the same manner as that in Example 9 except for using 378 mg of chloromethyl ethyl ether instead of 500 mg of chloromethyl methyl ether in Example 9, 680 mg of a crude product was obtained. Recrystallizing from a mixed solvent of ethyl acetate and n-hexane, 571 mg of the purified product was obtained with a yield of 70%.

The characteristics of the present compound thus obtained was as follows:

(1) elementary analysis;

|  | C (%) | H (%) | N (%) |
|---|---|---|---|
| theoretical: | 55.87 | 5.92 | 6.85 |
| experimental: | 55.7 | 5.8 | 6.8 |

TOXICOLOGICAL AND PHARMACOLOGICAL ACTIVITIES OF THE PRESENT COMPOUNDS

EXAMPLE 11

Acute toxicity of the present compounds were determined as follows.

Each of the present compounds was dispersed in a physiological saline solution. The dispersion was administered to an ICR-JCL mouse orally by a stomach sonde or intraperitoneally by injection at a predetermined amount.

After administration, the intoxication symptoms were continuously observed for a week and both survival and dead mice were autopsied to observe. $LD_{50}$ value was obtained from the cumulative mortality of the treated mice by applying the data to the Litchfield-Wilcoxon's graphical method. All of the present compounds gave $LD_{50}$ value of more than 10 g/kg in both oral and intraperitoneal administrations. The $LD_{50}$ value of the conventional penicillin as a comparative antibiotic is about 5 g/kg.

The results show that the present compound is a safe substance having a low toxicity.

EXAMPLE 12

Effect of the present compounds on the intestinal bacterial colonies was examined.

Each of the present compounds was orally administered to mice (one group consisting of five female ICR mice of 6-week-old) for two consecutive days at a dose of 500 mg/kg/day.

Before and on the first day after the administration, feces of each mouse was collected and diluted with an anerobic diluent (phosphoric buffer solution) of 100 times volume and ground. 0.1 ml of the diluted and ground feces was smeared on each culture medium shown in Table 1 and cultured aerobically or anaerobically (according to the anaerobic glove box method) under each condition shown in Table 1. The number of each bacterium shown in Table 1 was counted.

The results are shown in Table 2.

These results show that the present compounds do not affect the intestinal bacterial colonies in living bodies.

TABLE 1

| Culture medium and culture condition of bacteria | | |
|---|---|---|
| Bacterium | Culture medium | Culture condition |
| *Escherichia coli* | DHL agar | aerobic, 37° C., one day |
| *Pseudomonas aeruginosa* | NAC agar | aerobic, 37° C., one day |
| Streptococcus spp. | TATAC agar | aerobic, 37° C., one day |
| *Lactobacillus acidophilus* | LBS agar | anaerobic, 37° C., five days |
| *Lactobacillus bifidus* | BS agar | anaerobic, 37° C., five days |
| Bacteroides | NBGT agar | anaerobic, 37° C., five days |

TABLE 2

| | Logarithmic value of the number of bacterial cells per one gram of feces | | | | | |
|---|---|---|---|---|---|---|
| Example No. | E. coli | Ps. aeruginosa | Strept. spp. | L. acidophilus | L. bifidus | Bacteroides |
| 1 | 7.2 | <3.0 | 6.8 | 9.1 | 8.6 | 8.5 |
| 2 | 6.4 | <3.0 | 6.5 | 8.8 | 8.3 | 8.3 |
| 3 | 6.5 | <3.0 | 6.8 | 9.1 | 8.4 | 8.2 |
| 4 | 6.4 | <3.0 | 6.5 | 8.8 | 8.8 | 8.2 |
| 5 | 6.5 | 3.3 | 6.6 | 8.8 | 8.7 | 8.0 |
| 7 | 6.5 | <3.0 | 6.4 | 9.0 | 8.2 | 8.0 |
| 8 | 6.4 | <3.0 | 6.7 | 9.2 | 8.5 | 8.1 |
| 9 | 6.5 | 3.2 | 7.0 | 9.5 | 8.5 | 8.1 |
| 10 | 6.4 | <3.0 | 6.6 | 9.0 | 8.4 | 8.2 |
| Before administration | 6.4 | <3.0 | 6.8 | 9.0 | 8.4 | 8.3 |

EXAMPLE 13

Antibacterial activity of the present compounds was examined as follows.

Antibacterial activity of each of the present compounds was examined against the following two bacteria according to the standard method of Japan Society of Chemotherapy:

*Escherichia coli* IFO 12734 and

*Staphylococcus aureus* IAM 1011

Each bacterial strain was inoculated into the Mueller-Hinton's culture medium and cultured at 37° C. for 18 to 48 hours. The culture medium was diluted so as to contain $1 \times 10^6$ cells of the bacteria per one ml, and the obtained medium was used as the bacterial specimen.

Agar plates were prepared by adding one part by weight of each solution of the present compounds having a predetermined concentration to nine parts by weight of Mueller-Hinton's culture medium.

A loopful amount of the bacterial specimen prepared above was smeared to make a streak of about 2 cm on each agar plate and cultured at 37° C. for 18 to 24 hours. The minimum concentration for completely inhibiting proliferation of the bacteria (referred as MIC) was determined.

The results are shown in Table 3.

TABLE 3

| Example No. | MIC | |
|---|---|---|
| | E. coli | Staph. aureus |
| 1 | 200≦ | 0.39 |
| 2 | 6.25 | 0.1 |
| 3 | 12.5 | 0.78 |
| 4 | 12.5 | 0.78 |
| 5 | 6.25 | 0.1 |
| 6 | 100≦ | 12.5≦ |
| 7 | 100≦ | 12.5≦ |
| 8 | 100≦ | 12.5≦ |
| 9 | 25≦ | 12.5 |
| 10 | 25≦ | 12.5 |

EXAMPLE 14

The following experiment was carried out in order to prove that the present compound is activated in a living body.

As an enzyme for activating metabolism, a rat liver homogenate (S-9, manufactured by Oriental Yeast Company, Japan) was used in the following composition per one ml (hereinafter referred to as S-9 mix).

| S-9 | 0.5 ml |
|---|---|
| KCl | 3.3 μmol |
| MgCl$_2$.6H$_2$O | 8 μmol |
| Glucose-6-phosphate | 5 μmol |
| NADH | 4 μmol |
| NADPA | 4 μmol |
| 0.2 M phosphoric buffer solution (pH 7.4) | 0.5 ml |

0.1 ml of each solution of the present compounds at a concentration of 100 μg/ml was mixed with 0.9 ml of S-9 mix or 0.9 ml of 0.1M phosphoric buffer solution (as a control) and the obtained mixture was incubated at 37° C. for 20 min with shaking.

*Staphylococcus aureus* IAM 1011 was inoculated into a Mueller-Hinton's culture medium and cultured at 37° C. for 18 hours. The culture medium was adjusted to a cell concentration of 1×10$^8$ per one ml and mixed with 50 times by volume of Mueller-Hinton's agar culture medium to obtain an agar plate.

A penicillin cup of 8 mm in diameter was placed on the agar plate prepared above, and into the cup 0.1 ml of the mixture was introduced and allowed to stand at 4° C. for 2 hours and then cultured at 37° C. for 18 hours to measure the diameter of a circle in which the proliferation of bacteria was inhibited (proliferation-inhibiting circle). The results are shown in Table 4. In Table 4, the proliferation-inhibiting index is shown with the ratio (%) of the diameter of the proliferation-inhibiting circle obtained by using each of the present compounds to that obtained by using the comparative compound (conventional penicillin antibiotic).

| Index | % |
|---|---|
| − | 0 |
| ± | 0-1 |
| + | 1-33 |
| + + | 33-66 |
| + + + | 66-100 |

TABLE 4

| Example No. | Proliferation-inhibiting index (%) | |
|---|---|---|
| | Before adding S-9 mix | After adding S-9 mix |
| 1 | − | ± |
| 2 | + + | + + + |
| 3 | + + | + + + |
| 4 | + + | + + + |
| 5 | + + | + + + |
| 6 | + + | + + + |
| 9 | + | + + |
| 10 | + | + + |

As seen from Table 4, the antibacterial activity of the present compound is activated by an enzyme in a living body, although it itself shows a low antibacterial activity in the absence of an activating enzyme.

EXAMPLE 15

Effect of the present compounds on the infection was examined.

*Escherichia coli* IFO 12734 (1.4×10$^8$) was inoculated intraperitoneally to ddY-SPF mice (a group consisting of 20 mice). Just after and at 4 hours after the infection, each of the present compounds was administered orally at a dose of 500 mg/kg and the mortality of the mice due to the infection was observed for 7 days. More than 35% of the mice administered with the present compound survived even on the 7th day after the infection, while all mice without the administration with the present compound died on the 2nd day after infection.

The results show that the present compound is an effective medicine for oral administration against an infectious disease.

MANUFACTURE OF THE PHARMACEUTICAL PREPARATIONS

EXAMPLE 16

| (1) Tablet | |
|---|---|
| A tablet was prepared by a following composition in one tablet of 200 mg; the present compound of Example 1 | 175 mg |
| lactose | 16 mg |
| starch | 5 mg |
| hydroxypropylcellulose | 3 mg |
| magnesium stearate | 1 mg |

The present compound and lactose was mixed and then an aqueous solution of hydroxypropylcellulose was admixed, and the mixture was kneaded, dried and pulverized. Then magnesium stearate dispersed previously into starch was admixed and the mixture was made into a tablet by the conventional method for tabletting.

| (2) Granule | |
|---|---|
| A granule was prepared by a following composition; the present invention of Example 1 | 176 mg |
| lactose | 16 mg |

| -continued | |
|---|---|
| (2) Granule | |
| starch | 4 mg |
| hydroxypropylcellulose | 4 mg |

The present compound, starch and lactose were mixed, and an aqueous solution of hydroxypropylcellulose was admixed and the mixture was dried and pulverized. The pulverized material was sifted by 12 to 48 mesh sieves to obtain a granule.

What is claimed is:

1. A penicillin derivative represented by the formula (I):

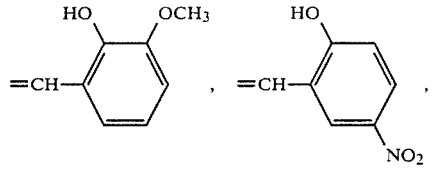

wherein R is

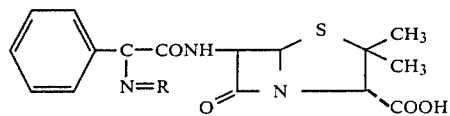

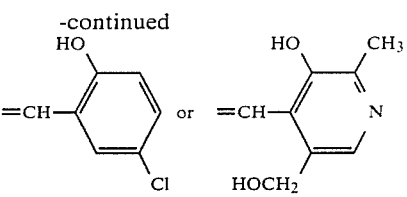

or a pharmaceutically acceptable salt thereof.

2. An antibacterial composition in dosage unit form comprising an effective amount of a penicillin derivative represented by the formula (I):

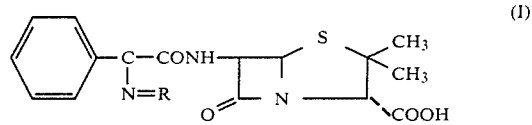

wherein R is

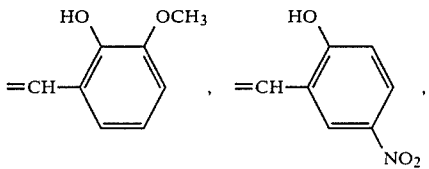

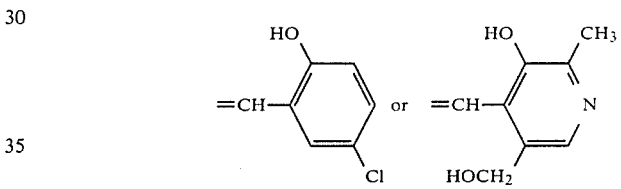

or a pharmaceutically acceptable salt thereof and a pharmaceutically acceptable carrier therefor.

* * * * *